US012594107B2

(12) United States Patent
Korman et al.

(10) Patent No.: US 12,594,107 B2
(45) Date of Patent: *Apr. 7, 2026

(54) MINIMALLY INVASIVE SURGERY OSTEOTOMY FRAGMENT SHIFTER, STABILIZER, AND TARGETER

(71) Applicant: WRIGHT MEDICAL TECHNOLOGY, INC., Memphis, TN (US)

(72) Inventors: Zachary Korman, St. Louis, MO (US); Shannon D. Cummings, Hernando, MS (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/251,959

(22) Filed: Jun. 27, 2025

(65) Prior Publication Data

US 2025/0318863 A1      Oct. 16, 2025

Related U.S. Application Data

(63) Continuation of application No. 19/021,690, filed on Jan. 15, 2025, now Pat. No. 12,364,528, which is a continuation of application No. 17/660,718, filed on Apr. 26, 2022, now Pat. No. 12,256,969.

(60) Provisional application No. 63/211,597, filed on Jun. 17, 2021.

(51) Int. Cl.
*A61B 17/17* (2006.01)
*A61B 17/66* (2006.01)
*A61B 17/88* (2006.01)

(52) U.S. Cl.
CPC ...... *A61B 17/8866* (2013.01); *A61B 17/1775* (2016.11); *A61B 17/66* (2013.01); *A61B 17/8897* (2013.01)

(58) Field of Classification Search
CPC ............ A61B 17/1775; A61B 17/1782; A61B 17/8866; A61B 2017/681
See application file for complete search history.

(56) References Cited

U.S. PATENT DOCUMENTS

| | | | | | |
|---|---|---|---|---|---|
| 3,835,849 | A | * | 9/1974 | McGuire | ............ A61B 17/1739 606/96 |
| 12,256,969 | B2 | * | 3/2025 | Korman | ................. A61B 17/66 |
| 12,364,528 | B2 | * | 7/2025 | Korman | ............. A61B 17/8866 |
| 2008/0009871 | A1 | * | 1/2008 | Orbay | ................ A61B 17/1728 606/70 |
| 2017/0014173 | A1 | * | 1/2017 | Smith | ................ A61B 17/1728 |
| 2020/0060698 | A1 | * | 2/2020 | Woodard | ........... A61B 17/1725 |

(Continued)

*Primary Examiner* — Nicholas W Woodall
(74) *Attorney, Agent, or Firm* — DUANE MORRIS LLP

(57)      ABSTRACT

A bone alignment system to correct a hallux valgus deformity includes a main body including an intramedullary (IM) hook, the IM hook including an end portion sized and configured to be inserted into an intramedullary canal of at least one of a first fragment or a second fragment of a bisected metatarsal; and a screw assembly including a screw threaded through the main body and a skin-interfacing portion attached to a first end of the screw, wherein the main body defines an aperture that extends through the main body and is sized and configured to guide a guide pin for anchoring the main body to the metatarsal.

19 Claims, 20 Drawing Sheets

(56)                    References Cited

U.S. PATENT DOCUMENTS

2021/0361330  A1 *  11/2021  McAleer ............ A61B 17/1775
2022/0192685  A1 *   6/2022  Gazonnet ........... A61B 17/8861
2022/0313287  A1 *  10/2022  Woodard ........... A61B 17/1775
2023/0013727  A1 *   1/2023  Korman ............. A61B 17/8897

* cited by examiner

700

MINIMALLY INVASIVE SURGERY OSTEOTOMY FRAGMENT SHIFTER, STABILIZER, AND TARGETER

CROSS-REFERENCE TO RELATED APPLICATION

This application is a continuation filed under 37 C.F.R. § 1.53 claiming the benefit under 35 U.S.C. § 120 of any and all applications for which a foreign or domestic priority claim is identified in the Application Data Sheet as filed with the present application, including U.S. patent application Ser. No. 19/021,690, filed Jan. 15, 2025, U.S. patent application Ser. No. 17/660,718, filed Apr. 26, 2022 (now U.S. Pat. No. 12,256,969), and claiming priority to U.S. Provisional Patent Application No. 63/211,597, filed Jun. 17, 2021, and are hereby incorporated by reference in accordance with 37 C.F.R. §§ 1.57; 1.97; and 1.98 in their entireties.

FIELD OF THE DISCLOSURE

The disclosed system and method relate to correcting anatomical structures. A bone alignment and screw drill targeting guide are provided for use in surgical procedures to correct hallux valgus deformity (i.e. bunions). The disclosure also provides an assembly that shifts, stabilizes, and targets osteotomy fragments during minimally invasive osteotomy surgery.

BACKGROUND OF THE INVENTION

Hallux valgus deformities occur when a metatarsal goes into a *varus* state (i.e., is pointed inwardly). In addition to being pointed inwardly, the metatarsal also may be rotated about its longitudinal axis such that the bottom of the bone is facing outwardly, which may result in the sesamoid being pointed outwardly when it should be located underneath the metatarsal. Correction of a bunion typically requires surgery and many techniques have been developed to correct hallux valgus deformities based on the deformity and the condition of the patient.

During a minimally invasive Chevron and Akin osteotomy (MICA) procedure for correcting hallux valgus deformity, a Chevron osteotomy is made in the first metatarsal bone separating the head portion of the first metatarsal from the remainder of the first metatarsal. The metatarsal head is then shifted laterally and fixed with two screws. K-wires are traditionally used to hold the metatarsal head at the intended translated position during the subsequent screw fixation procedure. Achieving the desired K-wire trajectory may be difficult. Therefore, a guiding instrument for setting the trajectory of the K-wire is desired.

Current technology does not allow easy lateral translation of the capital fragment after a distal first metatarsal osteotomy (made in the correction of Hallux Valgus) in such a way that the translation is controlled and maintained without requiring the user to rely on hand tools to hold the bones in place. Additionally, force applied by hand tools may cause the bones to shift relative to one another. Furthermore, current technology often does not allow reproducible and easy targeting of the capital fragment such that screws may follow an appropriate trajectory per state-of-the-art surgical techniques.

SUMMARY OF THE INVENTION

To overcome many of the aforementioned problems, embodiments of the invention provide a mechanism and method that controls lateralization of the capital fragment. This is accomplished via an intramedullary hook in the proximal fragment, a skin-interfacing wedge located against a capital fragment, and a screw mechanism to change the relative position of these two components. Additional stabilization is attained with a proximal skin-interfacing wedge, placed against the proximal fragment, that is adjustable via a screw mechanism. Furthermore, embodiments include a targeting arm for aiming at a target location in a certain proximity to the capital-fragment-engaging wedge such that wire sleeves may facilitate the placement of a guide pin along an idealized trajectory.

Accordingly, embodiments of the invention may ease lateral translation of the capital fragment after a distal first metatarsal osteotomy in such a way that the translation is controlled and maintained without requiring the user to rely on hand tools to hold the bones in place.

According to one embodiment of the invention, a system includes a first screw mechanism including: a first block; a first screw threaded through the first block and including a first skin-interfacing portion; and an intramedullary (IM) member extending from and attached to the first block and including an end portion configured to be inserted into an intramedullary canal of a first bone fragment, wherein a first lateral force is generated between the first skin-interfacing portion against a second bone fragment, adjacent to the first bone fragment, and a holding force provided by the end portion when the first screw is rotated and the end portion is located in the intramedullary canal.

A system of the invention may include a second screw mechanism including: a second block fixed to the first block; and a second screw threaded through the second block and including a second skin-interfacing portion, wherein a second opposing lateral force is generated between the second skin-interfacing portion against the first bone fragment and the holding force of the end portion when the second screw is rotated to move the second skin-interfacing portion toward the first bone fragment.

Another system of the invention may include a targeting arm attached to the first or the second skin-interfacing portions and including a first channel aligned to project a trajectory line to a target location on the second bone fragment, wherein the first and/or the second screws and the first and/or the second skin-interfacing portions include a bore configured such that a first anchor pin may be inserted through the bore and into an adjacent bone.

In another embodiment, the targeting arm may further include a second hole configured such that a second anchor pin may be inserted through the second hole to secure the targeting arm to a bone or a plurality of channels including the first channel that are aligned to each project a trajectory line to a plurality of target location on the second bone fragment.

In a further embodiment, a longitudinal axis along a length of the first channel is parallel to a longitudinal axis along a length of one of the other plurality of channels.

Another embodiment of the system includes a plurality of sleeves configured to be inserted through the plurality of channels and guide a wire to each of the plurality of target locations.

In an additional embodiment, the first block includes an anchor hole through the first block and configured such that a third anchor pin may be inserted through the anchor hole and into a bone adjacent to the portion.

According to another embodiment of the invention, a system may include a first block including an anchor hole; a first screw threaded through the first block; a first skin-interfacing portion attached to an end of the first screw; an intramedullary (IM) portion extending from and attached to the first block and including an end portion configured to be inserted into an intramedullary canal of a first bone fragment, wherein a lateral force is generated between the first skin-interfacing portion against a second bone fragment, adjacent to the first bone fragment, and a holding force provided by the end portion when the first screw is rotated and the end portion is located in the intramedullary canal.

In one embodiment, the first screw and the first skin-interfacing portion include a bore configured such that a first anchor pin may be inserted through the bore and into the second bone fragment.

In a further embodiment of the system a second anchor pin may be inserted through an anchor hole and into the first bone fragment adjacent to the intramedullary canal and adjacent to the end portion.

I another embodiment, the system may include a second screw mechanism having a second block fixed to the first block; and a second screw threaded through the second block and including a second skin-interfacing portion, wherein a second opposing lateral force is generated between the second skin-interfacing portion against the first bone fragment and the holding force of the end portion when the second screw is rotated to move the second skin-interfacing portion toward the first bone fragment. This system may further include a targeting arm attached to the first or the second skin-interfacing portions and including a first channel aligned to project a trajectory line to a target location on the second bone fragment.

In another embodiment, the first and/or the second screws and the first and/or the second skin-interfacing portions include a bore configured such that the first anchor pin may be inserted through the bore and into an adjacent bone or the targeting arm further includes a second hole configured such that a second anchor pin may be inserted through the second hole to secure the targeting arm to a bone.

In an further embodiment, the targeting arm includes a plurality of channels including the first channel that are aligned to each project a trajectory line to a plurality of target location on the second bone. In an embodiment, a longitudinal axis along a length of the first channel is parallel to a longitudinal axis along a length of one of the other plurality of channels.

According to another embodiment of the invention, a kit includes a first screw mechanism including: a first block; a first screw threaded through the first block; a first skin-interfacing portion attached to an end of the first screw; and an intramedullary (IM) portion extending from and attached to the first block and including an end portion configured to be inserted into an intramedullary canal; and a first anchor pin configured to be inserted through a bore in the first screw and the first skin-interfacing portion and into a second bone fragment that is adjacent to a first bone fragment.

A kit is provided including a second screw mechanism having a second block configured to be joined with the first block, a second screw threaded through the second block; and a second skin-interfacing portion attached to an end of the second screw.

Another kit may include a targeting arm configured to be attached to the first or the second skin-interfacing portions and the first bone and including a first channel aligned to project a trajectory line to a target location on the second bone fragment and a sleeve configured to be inserted through the first channel and guide a wire to the target location.

A kit may further include a second anchor pin configured to be inserted through an anchor hole in the first block and into the first bone fragment.

According to another embodiment of the invention, a method of correcting a hallux valgus deformity includes bisecting a metatarsal; inserting an intramedullary (IM) member that is attached to a first block of a first screw mechanism into an intramedullary canal of a proximal fragment of the metatarsal; aligning the first screw mechanism such that a longitudinal axis of a first screw threaded through the first block is substantially perpendicular to a longitudinal axis of the metatarsal; and rotating the first screw to generate a lateral force between a position of the IM member and a first skin-interfacing portion at an end of the first screw located against a capital fragment of the metatarsal or medial skin of the capital fragment of the metatarsal.

The method may further include joining a second block of a second screw mechanism to the first block such that a longitudinal axis of a second screw threaded through the second block is substantially parallel to the longitudinal axis of the first screw; and rotating the second screw such that a second skin-interfacing portion at an end of the second screw is against medial skin of the proximate fragment to generate a lateral force between the position of the IM member and the proximal fragment.

The method may also include inserting a first anchor pin through a bore through the first screw and first skin-interfacing portion and into the capital fragment; and turning the first screw to force lateralization of the capital fragment relative to the proximal fragment.

The method may further include attaching a targeting arm to one of the first or the second skin-interfacing portions; and inserting a second anchor pin through the targeting arm and into a bone.

The method may also include inserting a wire through the targeting arm, the proximal fragment, and into a target location of the capital fragment to fix the location of the capital fragment relative to the proximal fragment.

The method may further include inserting a first anchor pin through the first block and into the proximal fragment; inserting a second anchor pin through a bore through the first screw and first skin-interfacing portion and into the capital fragment; and turning the first screw to force lateralization of the capital fragment relative to the proximal fragment.

The above and other features, elements, characteristics, steps, and advantages of the invention will become more apparent from the following detailed description of preferred embodiments of the invention with reference to the attached drawings.

BRIEF DESCRIPTION OF THE DRAWINGS

The features and advantages of the invention will be more fully disclosed in, or rendered obvious by the following detailed description of the preferred embodiments, which are to be considered together with the accompanying drawings wherein like numbers refer to like parts and further wherein.

DETAILED DESCRIPTION OF PREFERRED EMBODIMENTS

Figure 1:
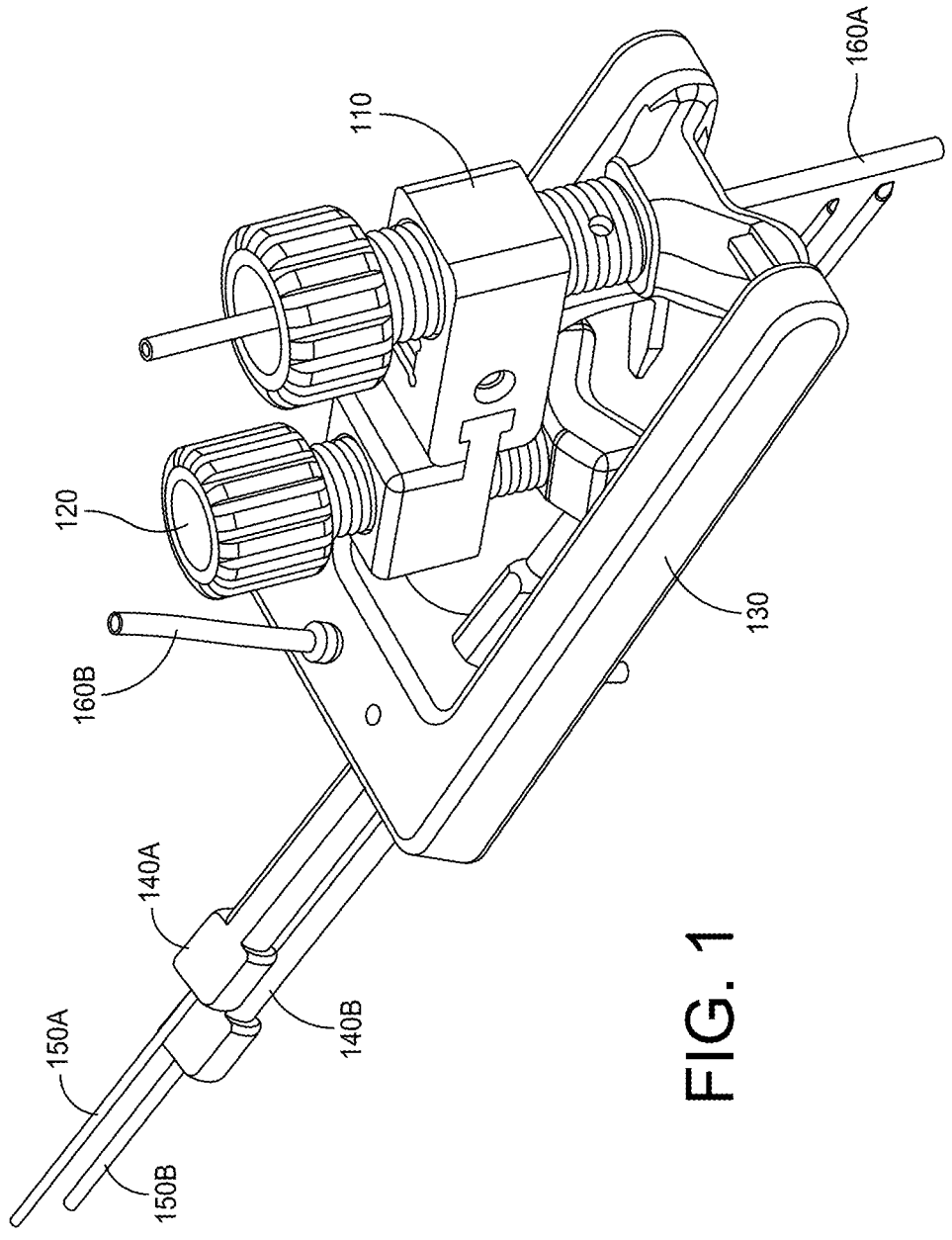
FIGS. 1 and 2 are views of a system according to an embodiment of the invention.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. Like elements have been given like numerical designations to facilitate an understanding of the subject matter.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations may exist based on manufacturing processes and/or other manufacturing requirements.

Figure 2:
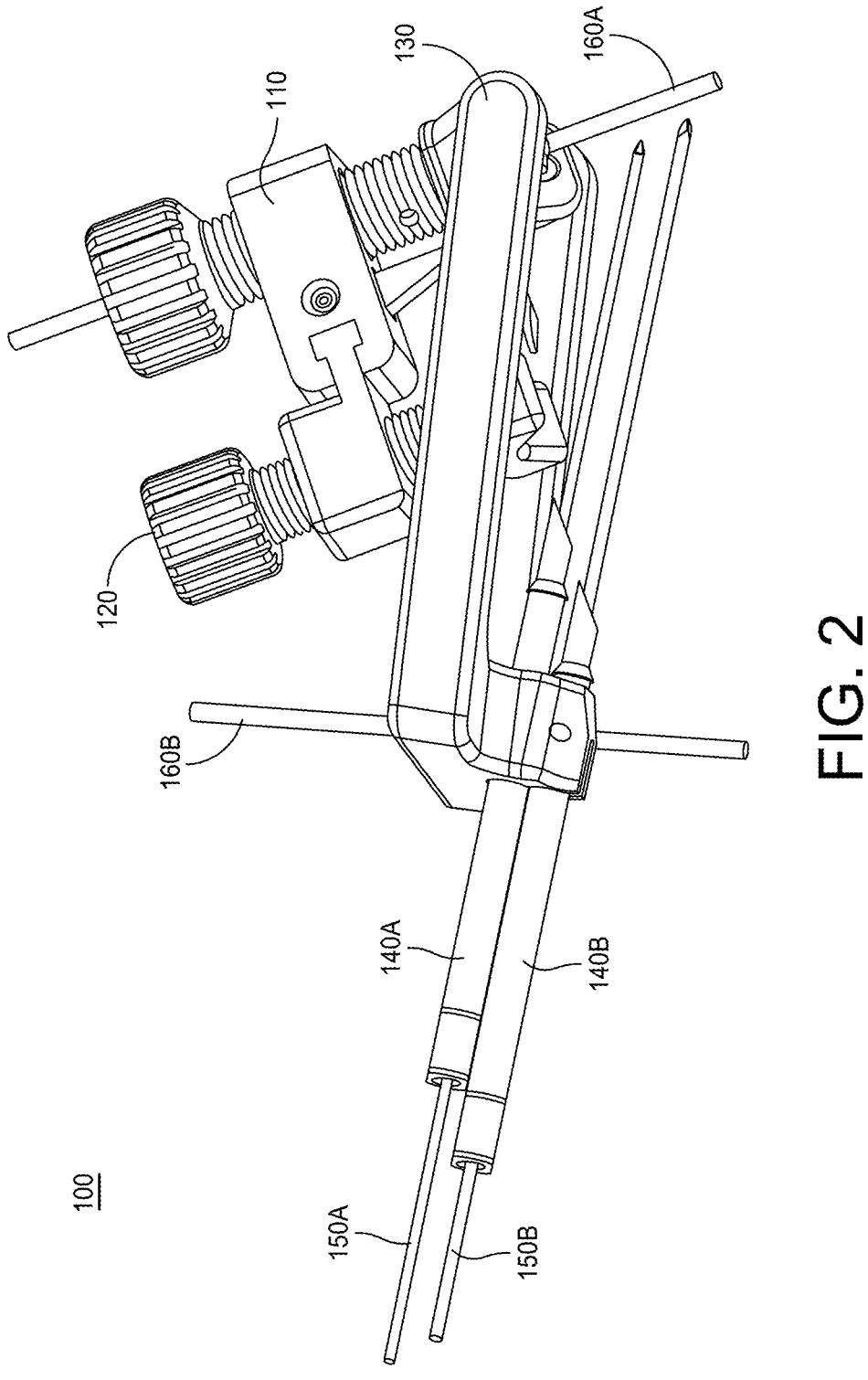

Referring to FIGS. 1 and 2, an exemplary system 100 is provided in accordance with an embodiment of the disclosure. The system 100 may be used to facilitate a distal metatarsal osteotomy for bunion correction via a minimally invasive surgical (MIS) procedure. FIGS. 1 and 2 show that the system 100 may include a first screw mechanism 110; a second screw mechanism 120; a targeting arm 130; sleeves 140A, 140B; K-wires 150A, 150B; and anchor pins 160A, 160B.

Figure 3:
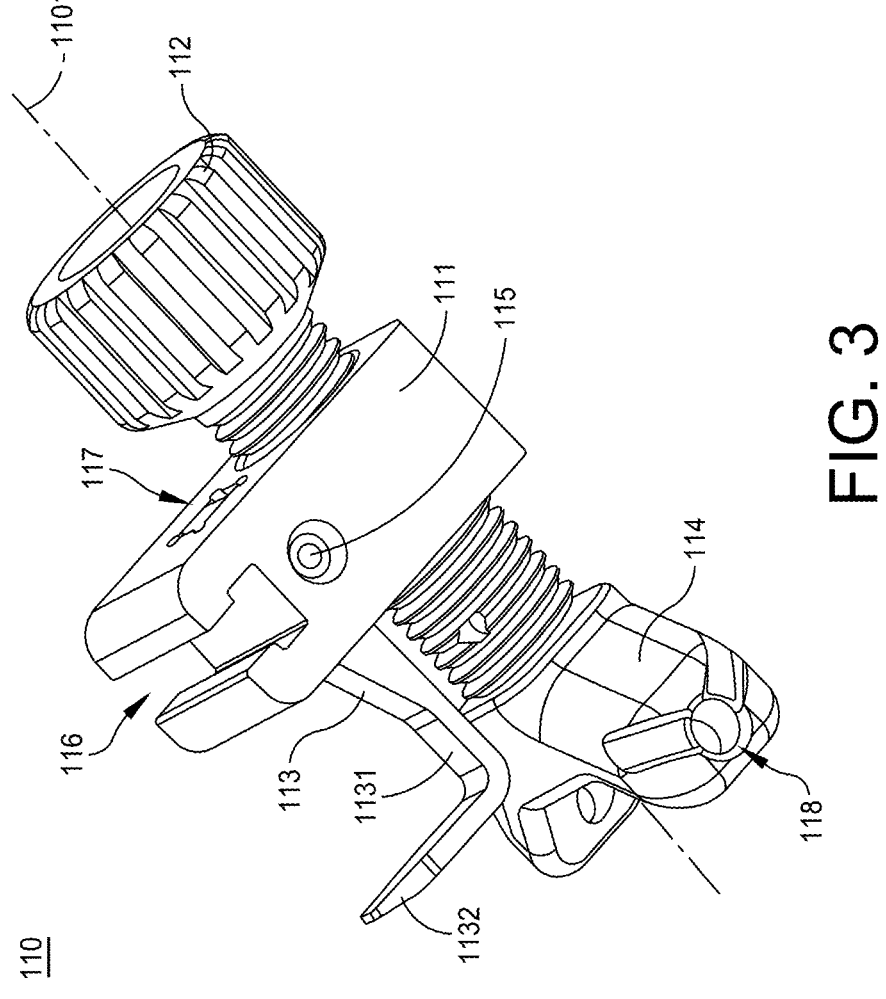
FIG. 3 shows a first screw mechanism of the system.

Referring to FIG. 3, the first screw mechanism 110 may include a first block 111 that includes a threaded bore to accept a first screw 112. As shown, the first screw 112 may include a threaded shaft that includes matching threads to mate with the threaded bore of the first block 111. The first screw 112 may include a head with a diameter that is larger than the shaft that may be used to grip the first screw 112 to provide a rotational force by hand or a tool. The first screw 112 may also include a bore (not shown) completely through along a longitudinal axis 1101 that may be used to locate and guide an anchor pin 160A as shown in FIGS. 1 and 2.

The first screw mechanism 110 may also include an intramedullary (IM) hook or member 113 that may be substantially L or J-shaped and attached to the first block 111. As shown in FIG. 3, the IM hook 113 may fit into a recess or groove in the first block 111 and be attached to the first block 111 via a fixation pin 115 that fixes the IM hook 113 to the first block 111. Optionally, the IM hook 113 may be fixed to the first block 111 with a hinge that allows the IM hook 113 to pivot with respect to the first block 111. Such a hinge may include a pin, screw, bolt, rivet, or any suitable mechanism that allows the IM hook 113 to rotate in relation to the first block 111.

The first block 111 may also include an aperture, window, or opening 117 that maximizes the recess into which the IM hook 113 is fixed and minimizes undesirable motion of the IM hook 113 with respect to the first block 111. As shown, the opening 117 exposes a first end portion of the IM hook 113. If in a hinged configuration, the aperture 117 may allow a user to view and/or rotate the first end portion of the IM hook 113 through the first block 111.

As shown, the IM hook 113 may be substantially flat with a rectangular cross section. Optionally, the IM hook 113 may be substantially cylindrical with a circular or oval cross section. The IM hook 113 may include a long length portion 1131 and a second end 1132 that is tapered or barbed. Optionally, the IM hook 113 may include portions that rotate with respect to each other. Optionally, the IM hook 113 may be configured to lock into place so that it does not rotate.

The first screw mechanism 110 may also include a first skin-interfacing wedge 114. Still referring to FIG. 3, the first skin-interfacing wedge 114 may be substantially U-shaped. Optionally, the first skin-interfacing wedge 114 may be substantially V or Y-shaped. As shown, the first skin-interfacing wedge 114 may be attached to an end portion of the shaft opposite to the head of the first screw 112. As such, the first skin-interfacing wedge 114 may be moved closer to or farther away from the first block 111 by rotating the first screw 112 with respect to the first block 111. The first skin-interfacing wedge 114 may be attached to the first screw 112 via a snap ring, bearing, peen, dowel pin, or any suitable means to allow the first skin-interfacing wedge 114 to substantially maintain its orientation with respect to the patient while the first screw 112 is rotated. The first skin-interfacing wedge 114 may also include a bore (not shown) completely through along a longitudinal axis 1101 that may be used to locate and guide an anchor pin 160A as shown in FIGS. 1 and 2. As shown, the first skin-interfacing wedge 114 may also include a recess, opening, or hole 118 in one or each of the legs of the wedge that are used to connect the first skin-interfacing wedge 114 to the targeting arm 130 as shown in FIGS. 1 and 2 and further discussed below.

Referring to Fig. FIG. 3, the first block 111 may include a slot, groove, or mortise 116 that is used to locate and join the second screw mechanism 120 to the first screw mechanism 110 as shown in FIGS. 1 and 2 and further discussed below.

Figure 4:
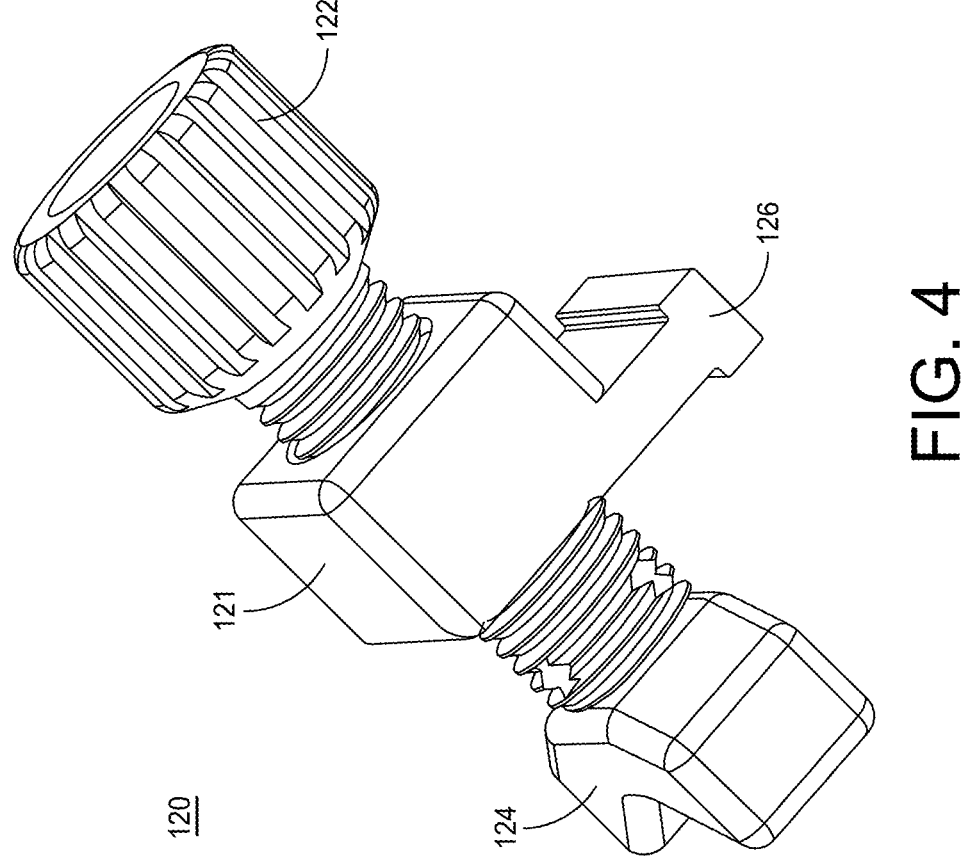
FIG. 4 shows a second screw mechanism of the system.

Referring to FIG. 4, that the second screw mechanism 120 may include a second block 121 that includes a threaded bore to accept a second screw 122 and a second skin-interfacing wedge 124 attached to a shaft of the second screw 122. As shown, the second screw 122 may include a threaded shaft that includes matching threads in which to be coupled with and allow the second screw 122 to rotate with relation to the second block 121. The second screw 122 may include a head with a diameter that is larger than the shaft that may be used to grip the second screw 122 to provide a rotational force by hand or a tool. Optionally, the second screw 122 may also include a bore (not shown) completely through along a longitudinal axis that may be used to locate and guide an anchor pin placed through the bore and into a patient's bone. Optionally, the second screw 122 may be interchangeable with or the same as the first screw 112.

Referring to FIGS. 3 and 4, the second skin-interfacing wedge 124 may be shaped similar to the first skin-interfacing wedge 114. That is, the second skin-interfacing wedge 124 may be substantially U-shaped. Optionally, the second skin-interfacing wedge 124 may be substantially V or Y-shaped. Like the first skin-interfacing wedge 114, the second skin-interfacing wedge 124 may be attached to an end portion of the shaft opposite to the head of the second screw 122. As such, the second skin-interfacing wedge 124 may be moved closer to or farther away from the second block 121 by rotating the second screw 122 with respect to the second block 121. The second skin-interfacing wedge 124 may be attached to the second screw 122 via a snap ring, bearing, peen, dowel pin, or any suitable means to allow the second skin-interfacing wedge 124 to substantially maintain its orientation with respect to the patient while the second screw 122 is rotated. Optionally, the second skin-interfacing wedge 124 may also include a bore (not shown) completely through along a longitudinal axis that may be used to locate and guide an anchor pin placed through and into a patient's bone. Optionally, the second skin-interfacing wedge 124 may also include a recess, opening, or hole in each of the legs of the wedge that are used to connect the second skin-interfacing wedge 124 to the targeting arm or other structure. Optionally, the second skin-interfacing wedge 124 may be interchangeable with or the same as the first skin-interfacing wedge 114.

Referring to FIG. 4, the second block 121 may include a protrusion, projection, or tendon 126 that is used to locate and join the second screw mechanism 120 to the first screw mechanism 110 as shown in FIGS. 1 and 2. Although shown as substantially T-shaped, the structure for joining the first block 111 to the second block 121 may be a tapered dovetail or any other shape suitable for interlocking. Optionally, this joining structure may include holes and pins or any other suitable fastening and joining system. Also, optionally, the first screw mechanism 110 and the second screw mechanism 120 may be threaded through a one block structure in effect combining the features of the first block 111 and the second block 121.

Figure 5:
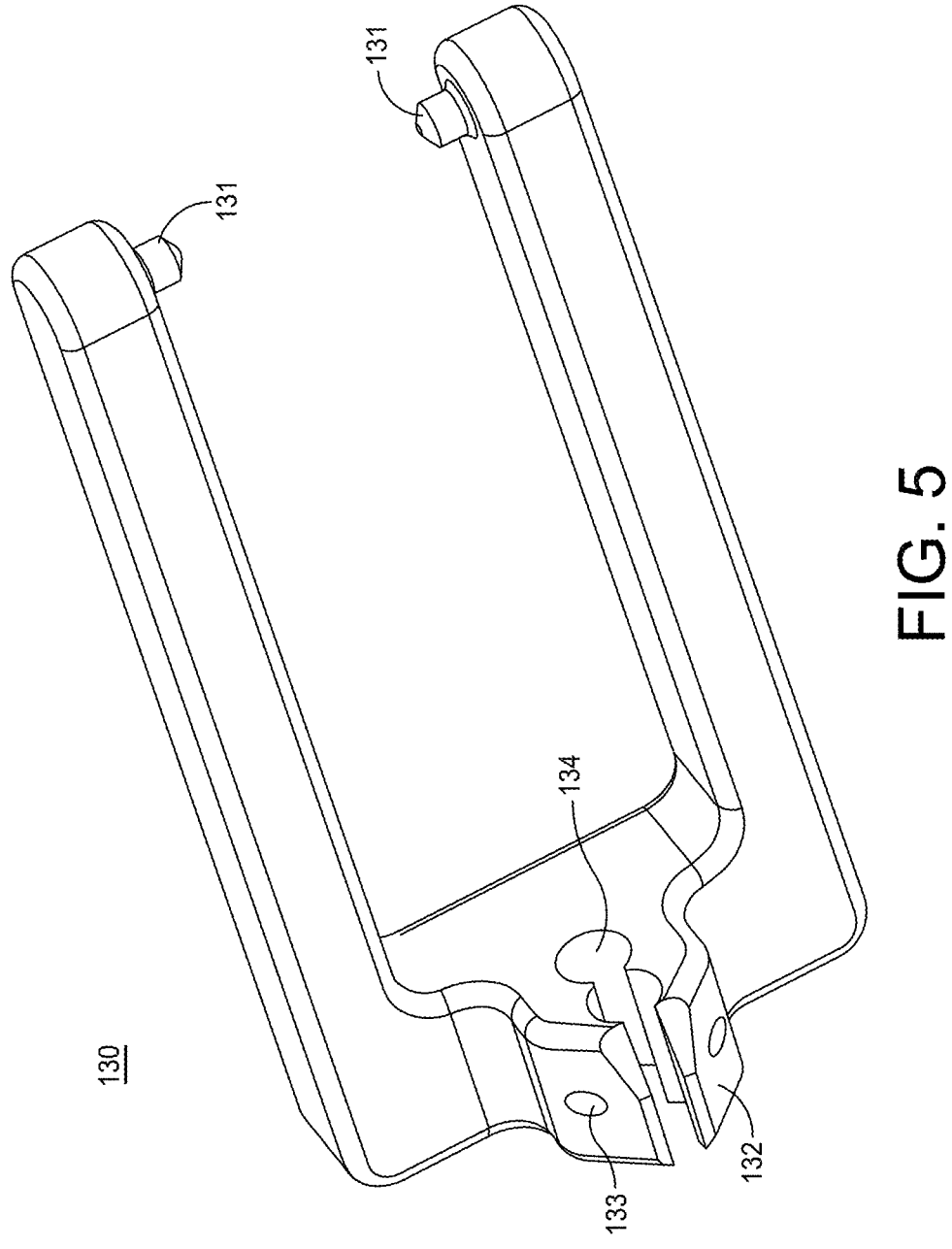
FIG. 5 shows a targeting arm of the system.
Figure 6:
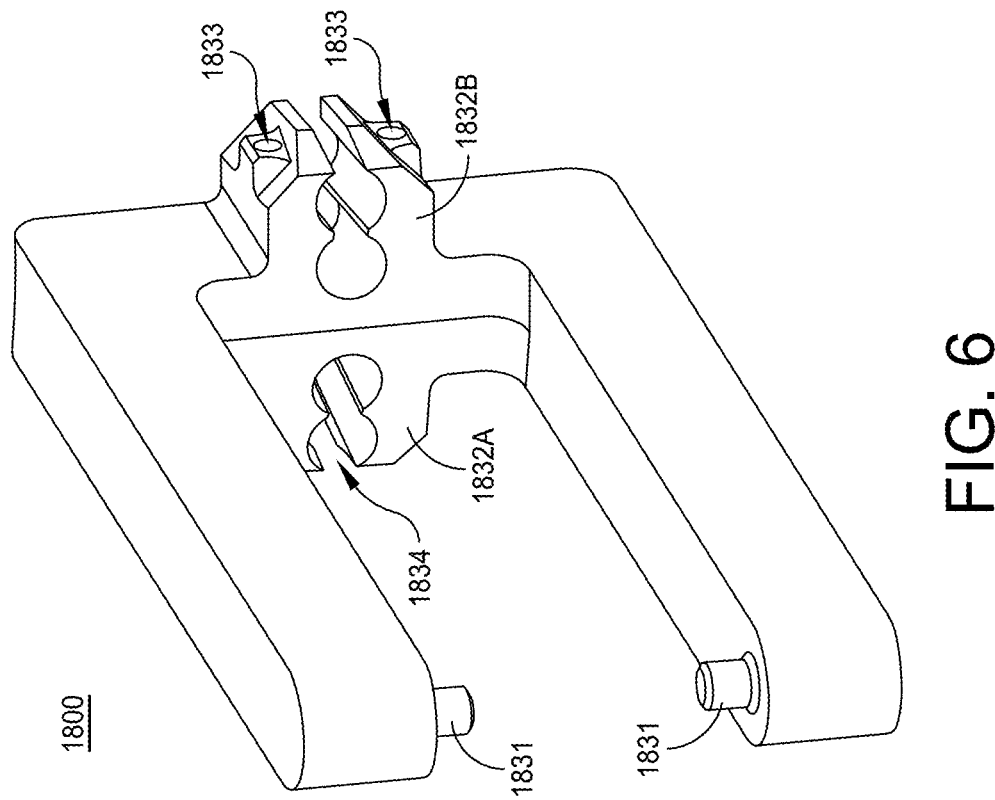
FIGS. 6 and 7 show alternative targeting arms.

Referring to FIG. 5, the targeting arm 130 may be substantially and symmetrically U-shaped with two legs that may extend longer than a length of a base. Two opposing protrusions, detents, or tabs 131 may be located one each on corresponding legs and arranged to fit into or mate with the holes 118 a skin-interfacing wedge. Outward force on the legs of the targeting arm 130 may be provided to open the distance between the legs so that the tabs 131 may clear the width of the skin-interfacing wedge so the tabs 131 may be oriented in the holes 118 and retained by a spring force created by the shape of the targeting arm 130. This arrangement allows the first screw mechanism 110 to attach to the target arm 130 while allowing the targeting arm 130 and first skin-interfacing wedge 114 to rotate with respect to each other about a longitudinal axis through the two tabs 131. The targeting arm 130 may include an integral protrusion arranged as a guiding mechanism 132. The guiding mechanism 132 may include one or more apertures or through holes 133 that extend through the guiding mechanism 132 and the base of the U-shaped structure. The through holes 133 may be used to align and guide one or more anchor pins 160B as shown in FIGS. 1, 2, and 6. The guiding mechanism 132 may also include one or more channels 134 that may be used to align and guide sleeves 140A, 140B to route K-wires 150A, 150B as shown in FIGS. 1, 2, and 6. The first and second screw mechanisms 110, 120, and the targeting arm 130 may be made from plastic, metal, metal alloy, composite, ceramic, or any other suitable material or combinations thereof. Any or all of the portions of the first and second screw mechanisms 110, 120, and the targeting arm 130 may be made via casting, molding, machining, injection molding, 3D printing, any other suitable manufacturing process, or combinations thereof.

Referring to FIG. 6, an alternative targeting arm 1800 is provided that is similar to targeting arm 130 but, the targeting arm 1800 may be substantially and symmetrically U-shaped with two legs extending longer than a length of a base. Two opposing protrusions, detents, or tabs 1831 may be located one each on corresponding legs and arranged to fit into or mate with the holes 118 of a skin-interfacing wedge as previously described. The targeting arm 1800 may include two integral protrusions arranged as guiding mechanism 1832A and 1832B. The guiding mechanisms 1832A and 1832B may be located on opposite sides of the targeting arm 1800. Each guiding mechanism 1832A, 1832B may include one or more apertures or through holes 1833 that extend through the guiding mechanism, the base of the U-shaped structure, and the other guiding mechanism. The through holes 1833 may be used to align and guide a guide pin as previously shown and discussed. The guiding mechanisms 1832A, 1832B may also include one or more bores 1834 that may be used to align and guide sleeves to route k-wires as previously shown and discussed. Optionally, the longitudinal axis of each of the bores 1834 may be aligned at different angles relative to the targeting arm 1800 to allow for different targeting options during surgery.

Figure 7:
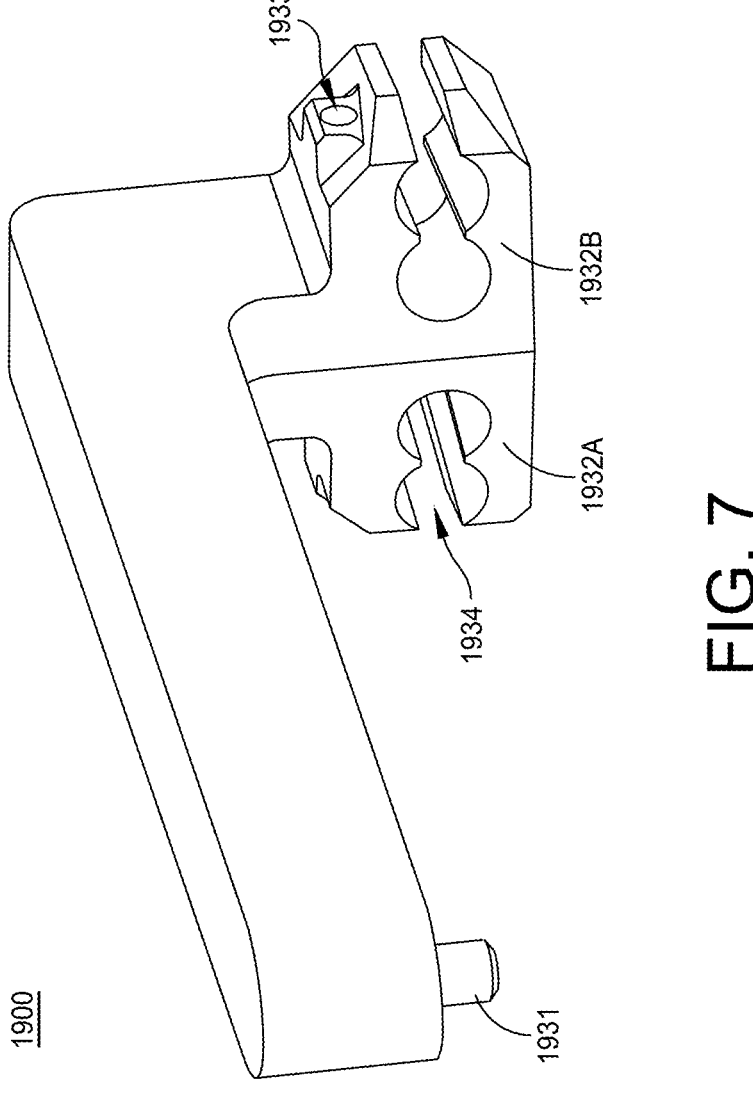

Referring to FIG. 7, an alternative targeting arm 1900 may be substantially and symmetrically L-shaped with one leg extending longer than another leg. A protrusion, detent, or tab 1931 may be located at the end of one of the legs and arranged to fit into or mate with one of the holes 118 of a first skin-interfacing wedge as previously described. Targeting arm 1900 may include two integral protrusions arranged as guiding mechanism 1932A and 1932B. Optionally, the targeting arm 1900 may include only one guiding mechanism. Each guiding mechanism 1932A, 1932B may include one or more apertures or through holes 1933 that extend through the guiding mechanism, one leg of the L-shaped structure, and the other guiding mechanism. The guiding mechanisms 1932A, 1932B may also include one or more bores 1934.

Figure 8:
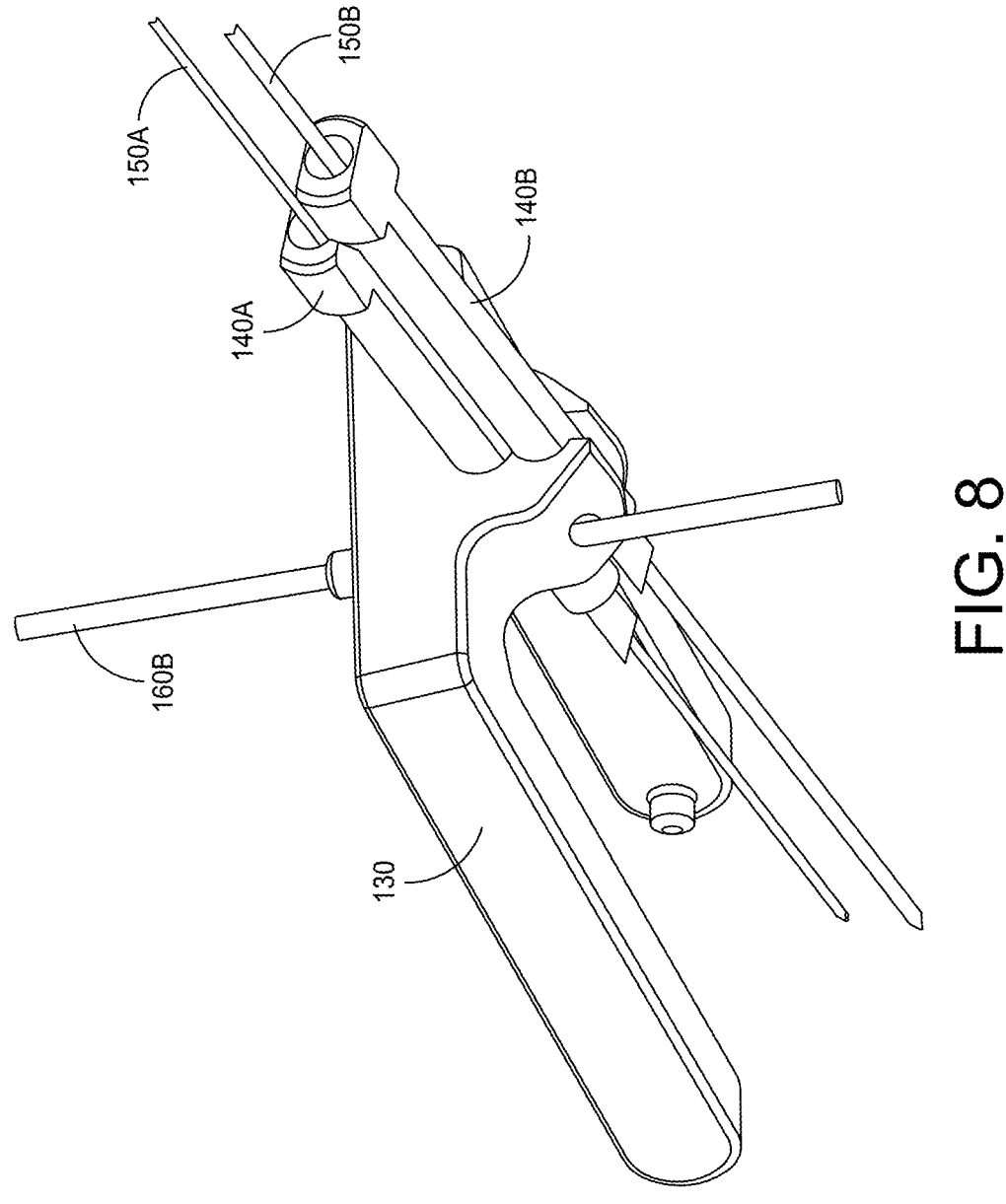
FIG. 8 shows a targeting arm assembly of the system.

Referring to FIG. 8, an assembly is provided that includes the targeting arm 130, two sleeves 140A, 140B, two K-wires 150A, 150B through corresponding sleeves 140A, 140B and the anchor pin 160B.

Figure 9:
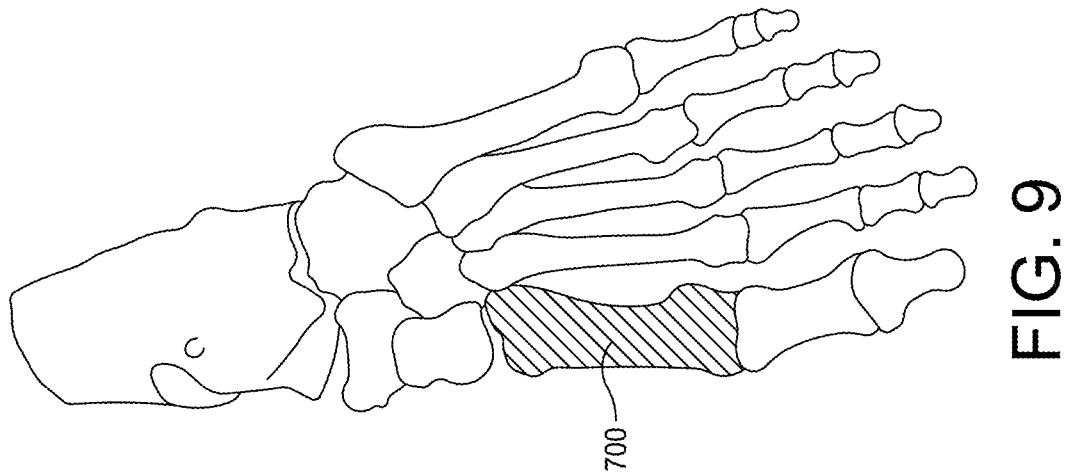
FIG. 9 is an image of a human foot.

As previously mentioned, the system 100 is designed to be used in surgery during the correction of Hallux Valgus in the first metatarsal. FIG. 9 is a skeletal image of the underside of a human's right foot with the first metatarsal 700 highlighted. FIGS. 10-19 describe how the system 100 is to be used. Although FIGS. 10-19 include skeletal images of a patient's foot, it should be understood that the first and second skin-interfacing wedges 114, 124 and the targeting arm 130 are meant to contact the outside surface of the patient's skin, which is not depicted in the drawings.

Figure 10:
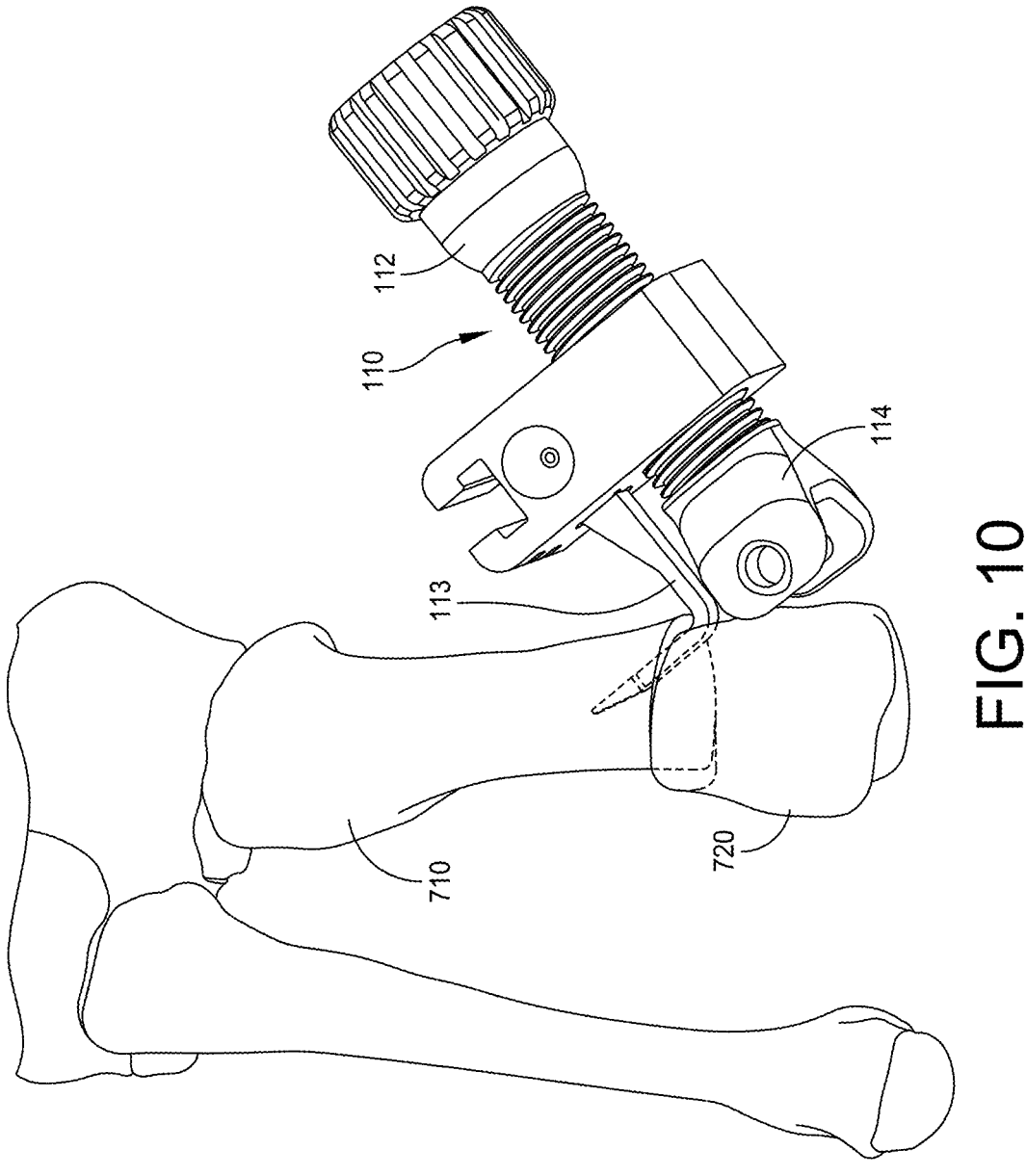
FIGS. 10-19 show how the system is assembled and used.
Figure 11:
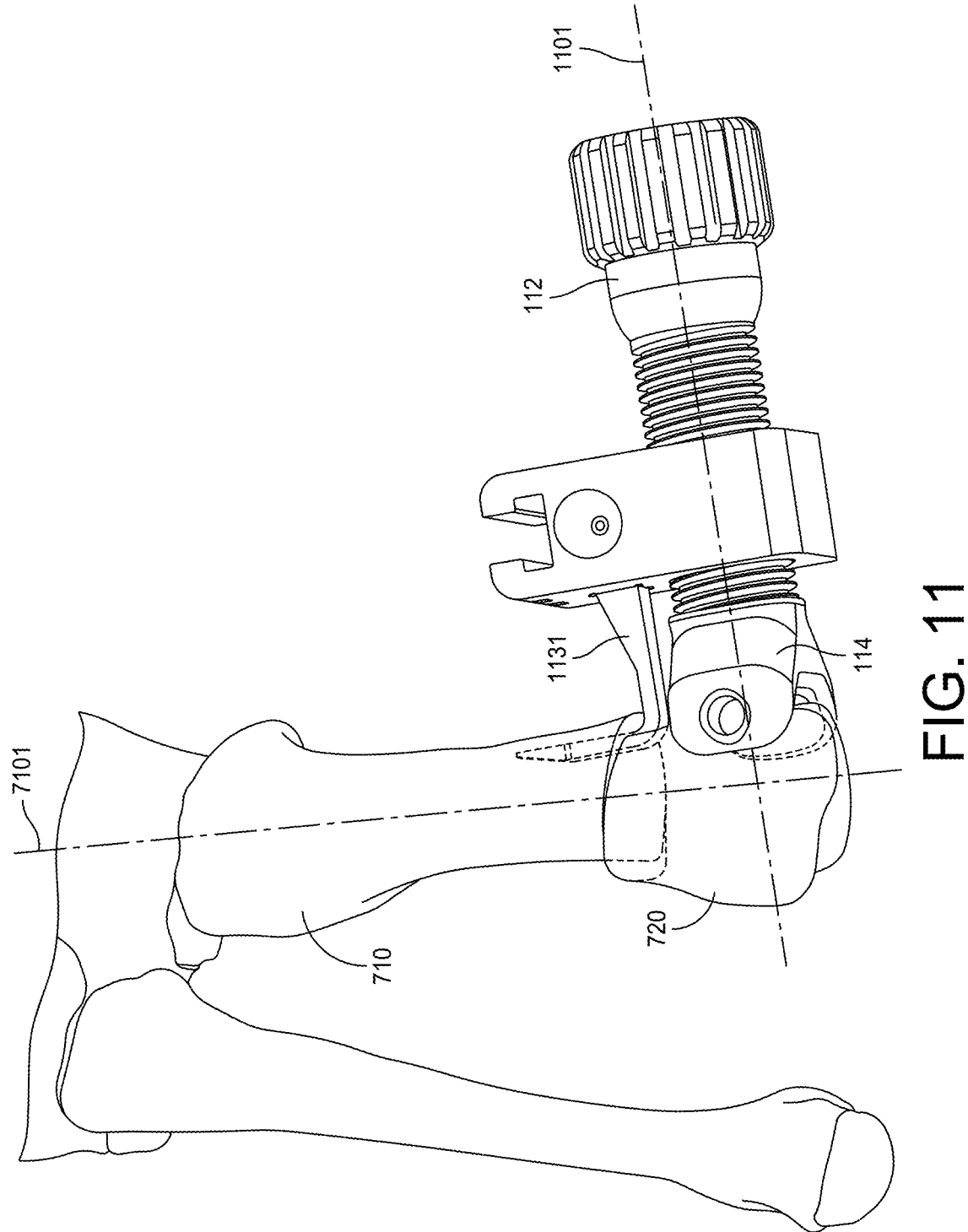

Referring to FIG. 10, after forming an incision to bisect the first metatarsal, the IM hook 113 of the first screw mechanism 110 is inserted into the IM canal of the proximal fragment 710 of the patient's first metatarsal while the first skin-interfacing wedge 114 is used to pivot the first screw mechanism 110 against the patient's skin outside the capital fragment 720. The orientation of the first screw mechanism 110 is adjusted by rotating the first screw 112 such that a long-length portion 1131 of the IM hook 113 and a longitudinal axis 1101 through the first skin-interfacing wedge 114 and the first screw 112 are aligned substantially perpendicular to a longitudinal axis 7101 of the first metatarsal, as shown in FIG. 11.

Figure 12:
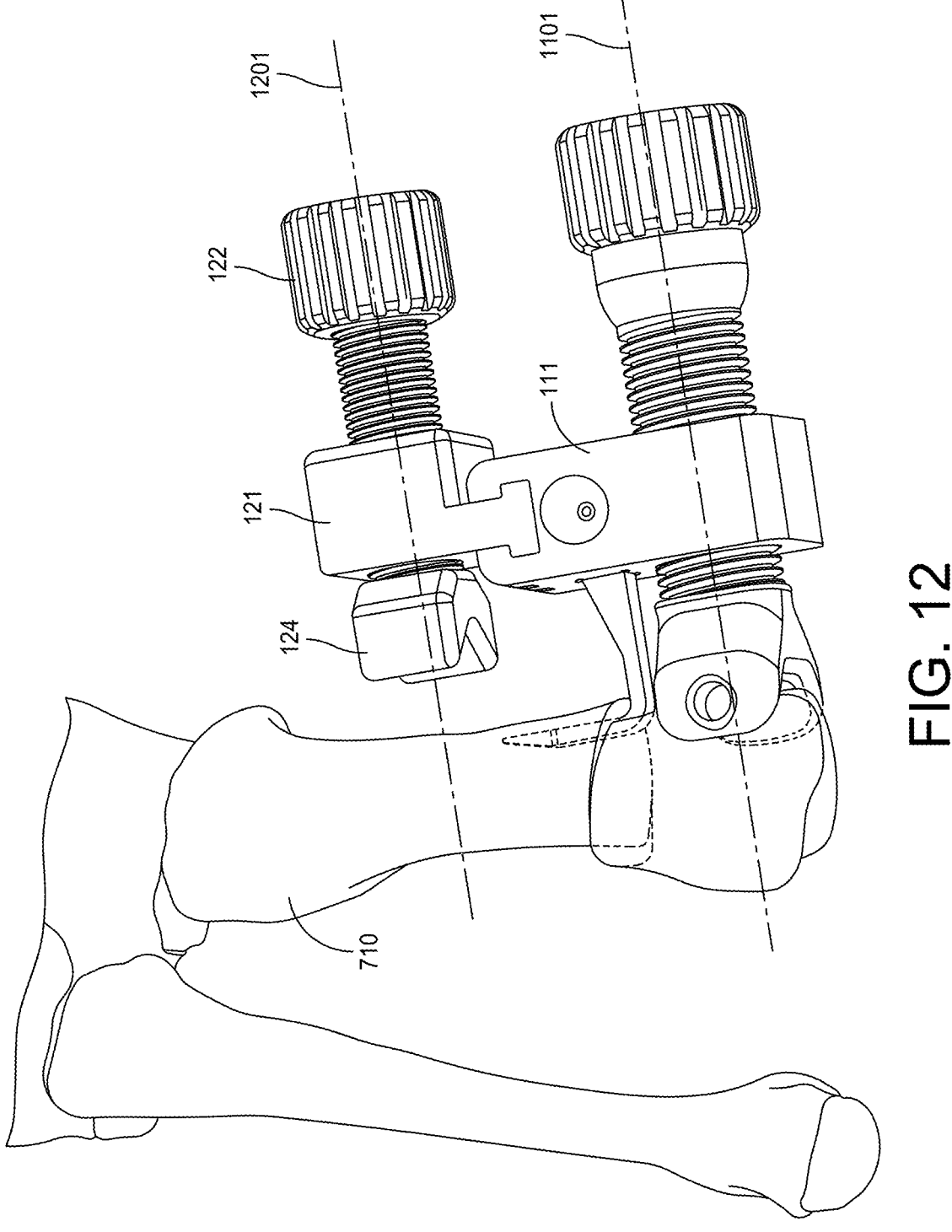
Figure 13:
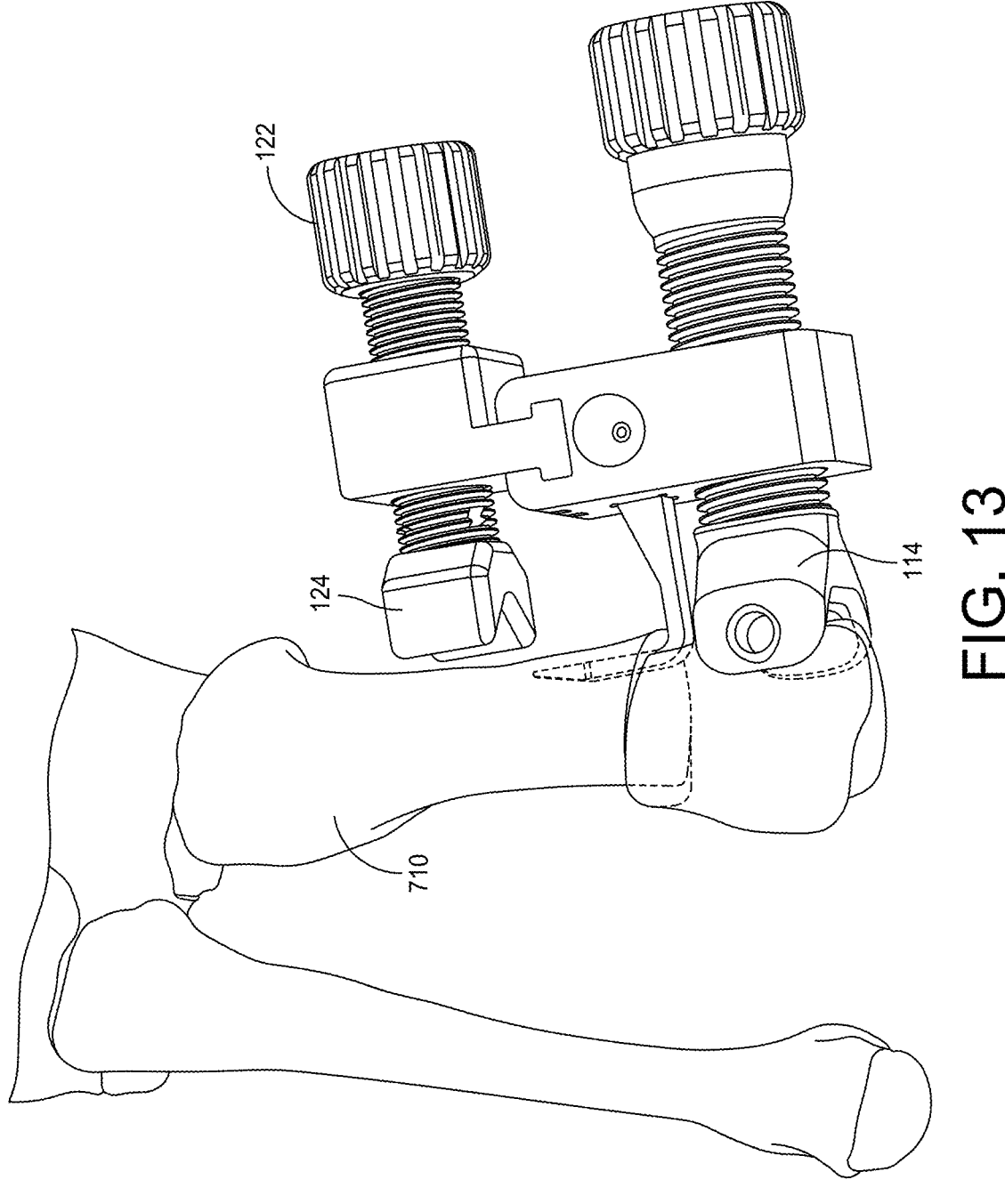

Referring to FIG. 12, the second block 121 of the second screw mechanism 120 is joined with the first block 111 of the first screw mechanism 110 to align a longitudinal axis 1201 through the second skin-interfacing wedge 124 and the second screw 122 to be substantially parallel to the longitudinal axis 1101 through the first skin-interfacing wedge 114 and the first screw 112. This positioning allows the system 100 to be stabilized against the medial skin/cortex of the patient's proximal fragment. The second screw 122 is then turned to ensure the second wedge 124 is firmly against the skin along the patient's proximal fragment 710, as shown in FIG. 13. This provides a force opposing the holding force of the IM hook 113 to stabilize the orientation of the first block 111 relative to the proximal fragment 710.

Figure 14:
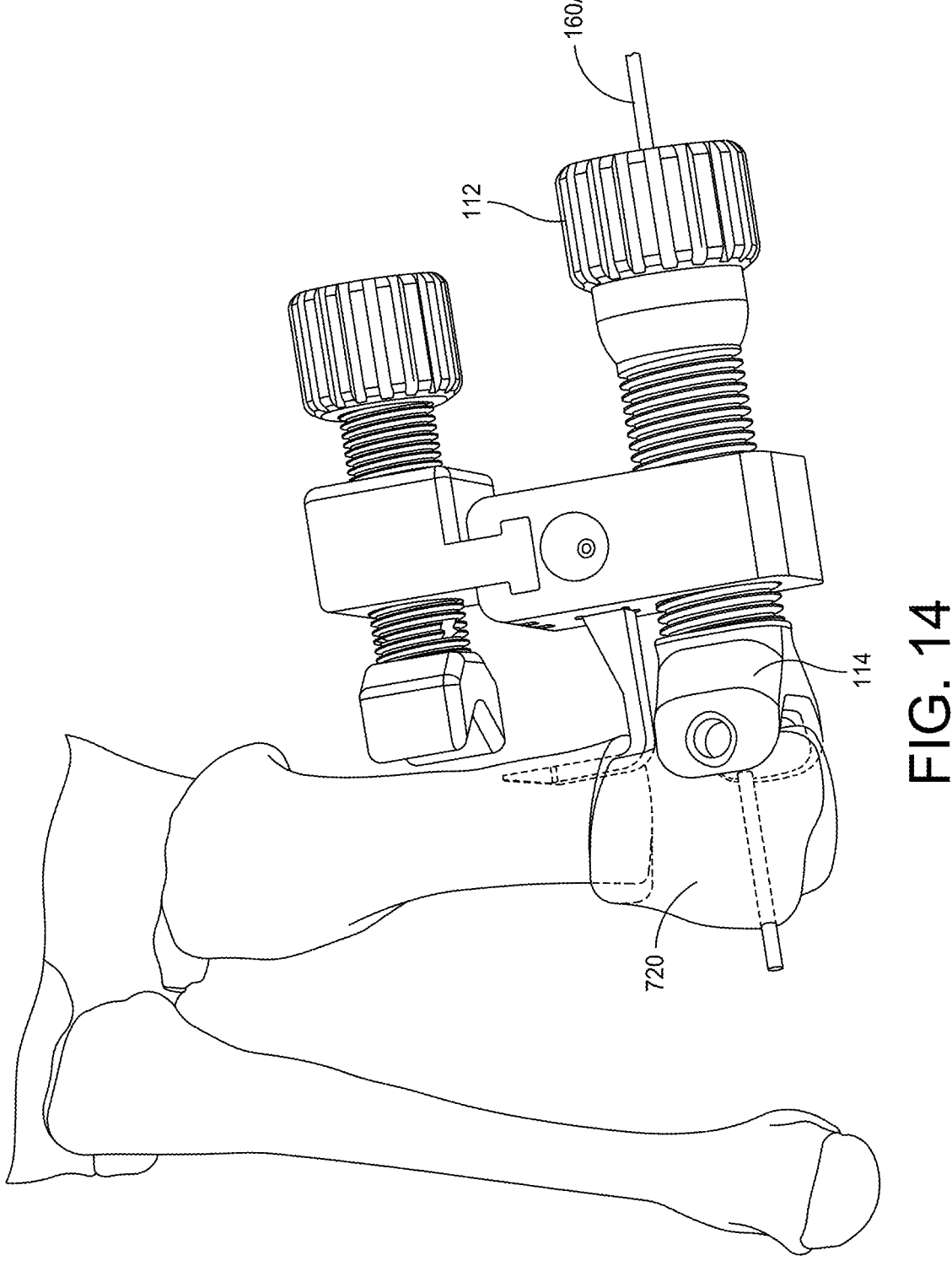
Figure 15:
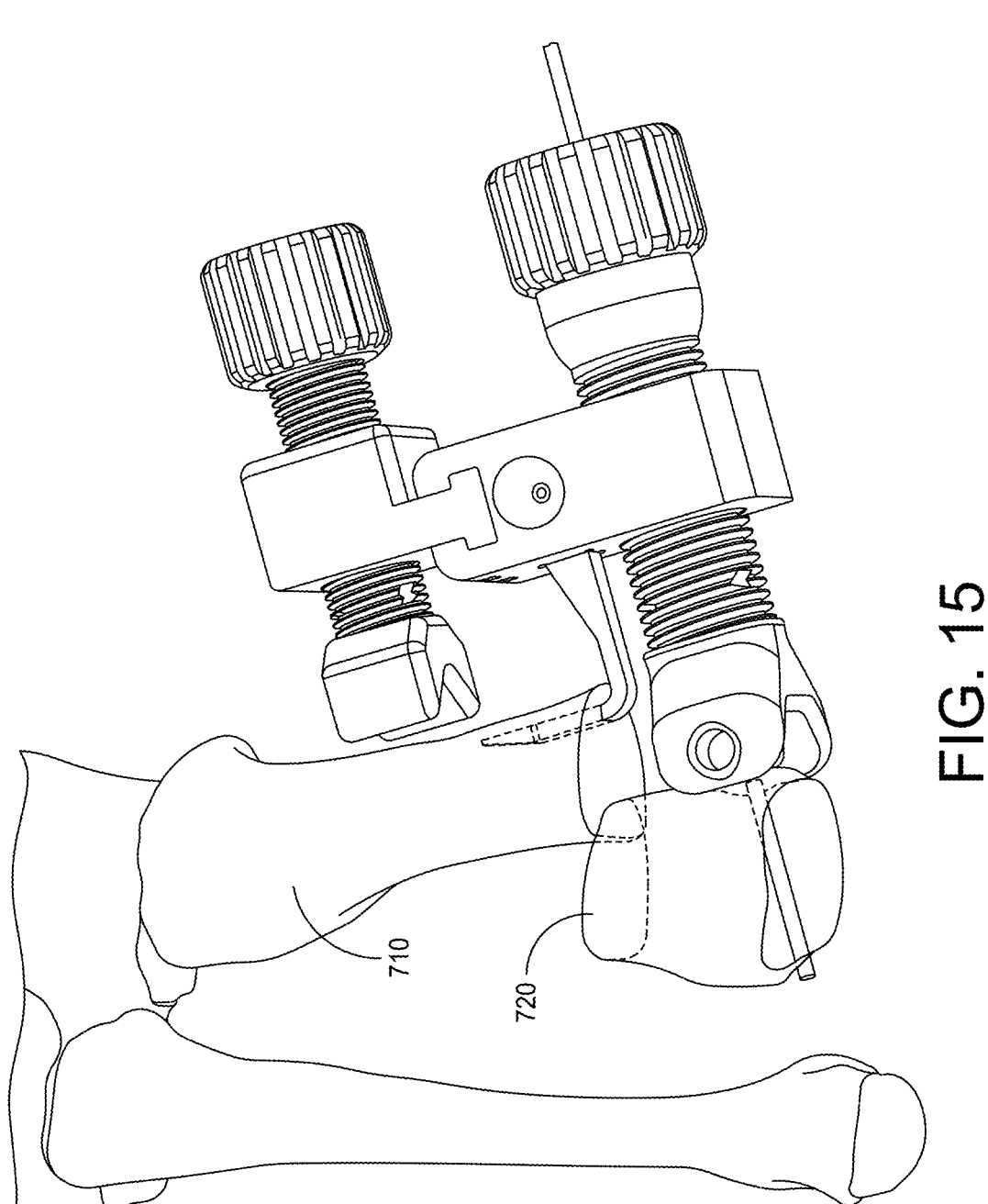

Referring to FIG. 14, an anchor pin 160A may then be inserted through the cannulated bore of the first screw 112 and the first skin-interfacing wedge 114 and into the capital fragment 720 to anchor the capital fragment 720. After the anchor pin 160A is inserted, the first screw 112 may be turned. This provides a lateral force opposing the holding force of the IM hook 113 to the proximal fragment 710 enforcing lateralization of the capital fragment 720 relative to the proximal fragment 710, as shown in FIG. 15, which is stabilized against undesired elevation/planarization, inversion/eversion, and pronation/supination. If supination of the capital fragment 720 is desired, an additional, guide pin (not shown) may be inserted into the capital fragment 720 and used as a "joystick" to achieve the desired supination position prior to insertion of the anchor pin 160A through the first screw mechanism 110 and into the capital fragment 720.

Figure 16:
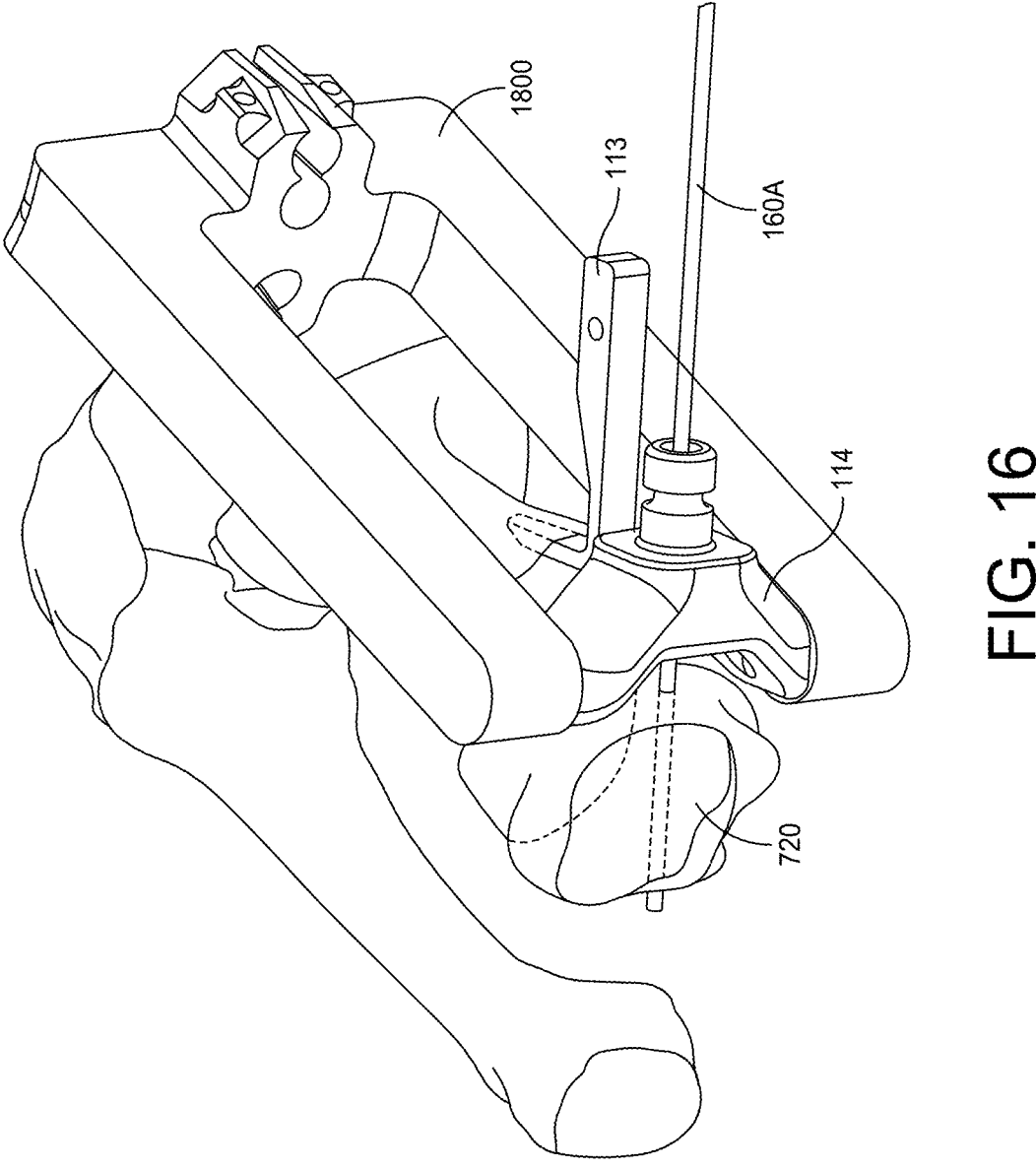
Figure 17:
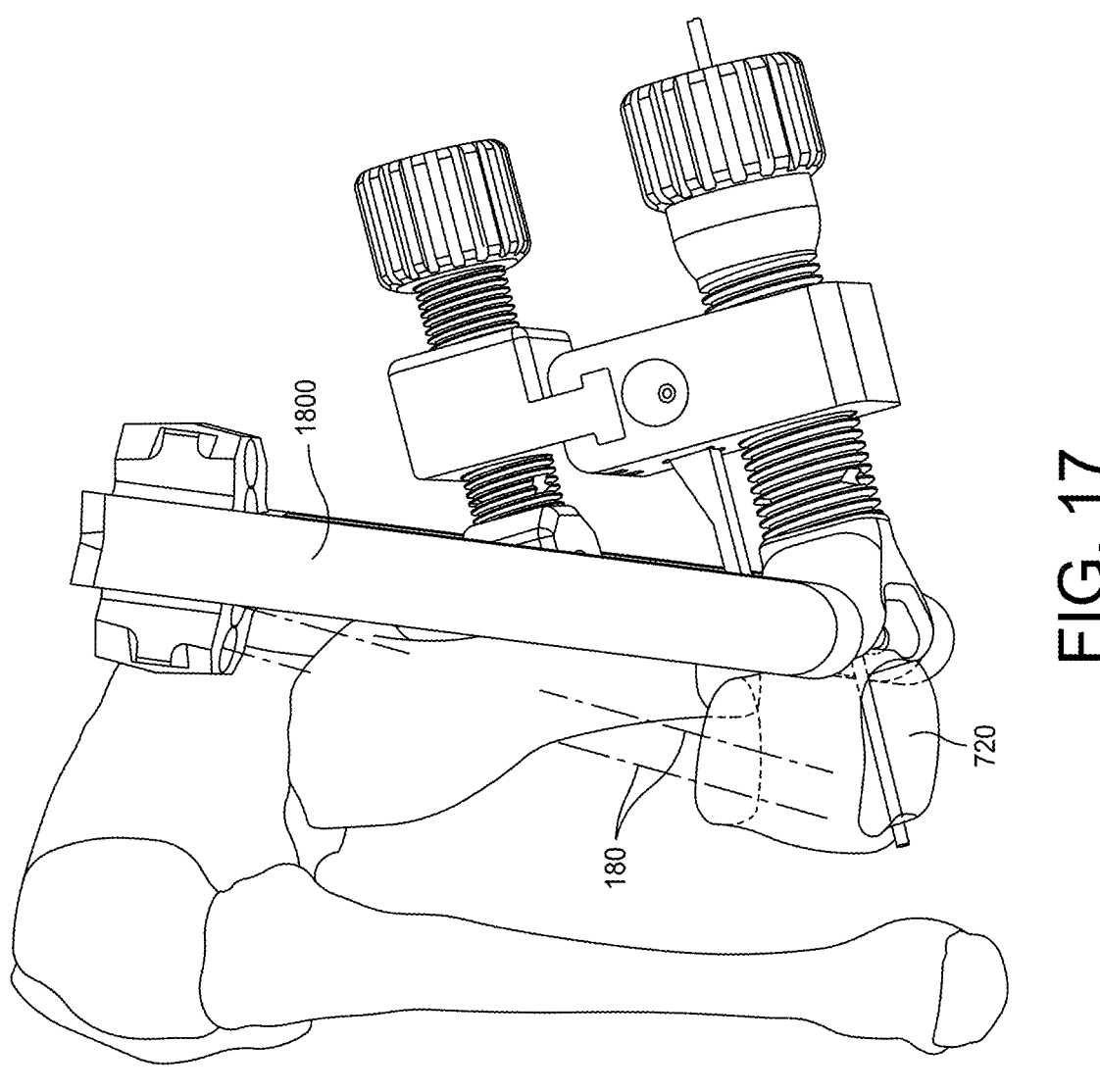

Referring to FIGS. 16 and 17, the targeting arm 1800 may then be attached to the first skin-interfacing wedge 114 of the assembly. FIG. 16 shows the relative orientation of the targeting arm 1800, the IM hook 113, the first skin-interfacing wedge 114, the capital fragment 720, and the anchor pin 160A. The targeting arm 1800 is designed to target at least one specified location a certain distance lateral to the pushing surface of the first skin-interfacing wedge 114. FIG. 17 includes projected trajectory lines 180 to show two target locations. Optionally, the targeting arm 1800 may be attached to the second skin-interfacing wedge 124.

During surgery, it is possible to use multiple targeting arms that have slightly more medial or lateral targeting locations depending on specific patient anatomy. Optionally, a targeting arm configuration may include additional holes that may be parallel to and directly superior to channels 134. These additional holes may be sized to accept guide pins, that would allow a user to x-ray the patient's foot and determine the guide trajectory that the targeting arm 1800 is providing. The user may then decide to proceed, or to switch to a targeting arm that provides more medially or more laterally aiming of the guide trajectory.

Figure 18:
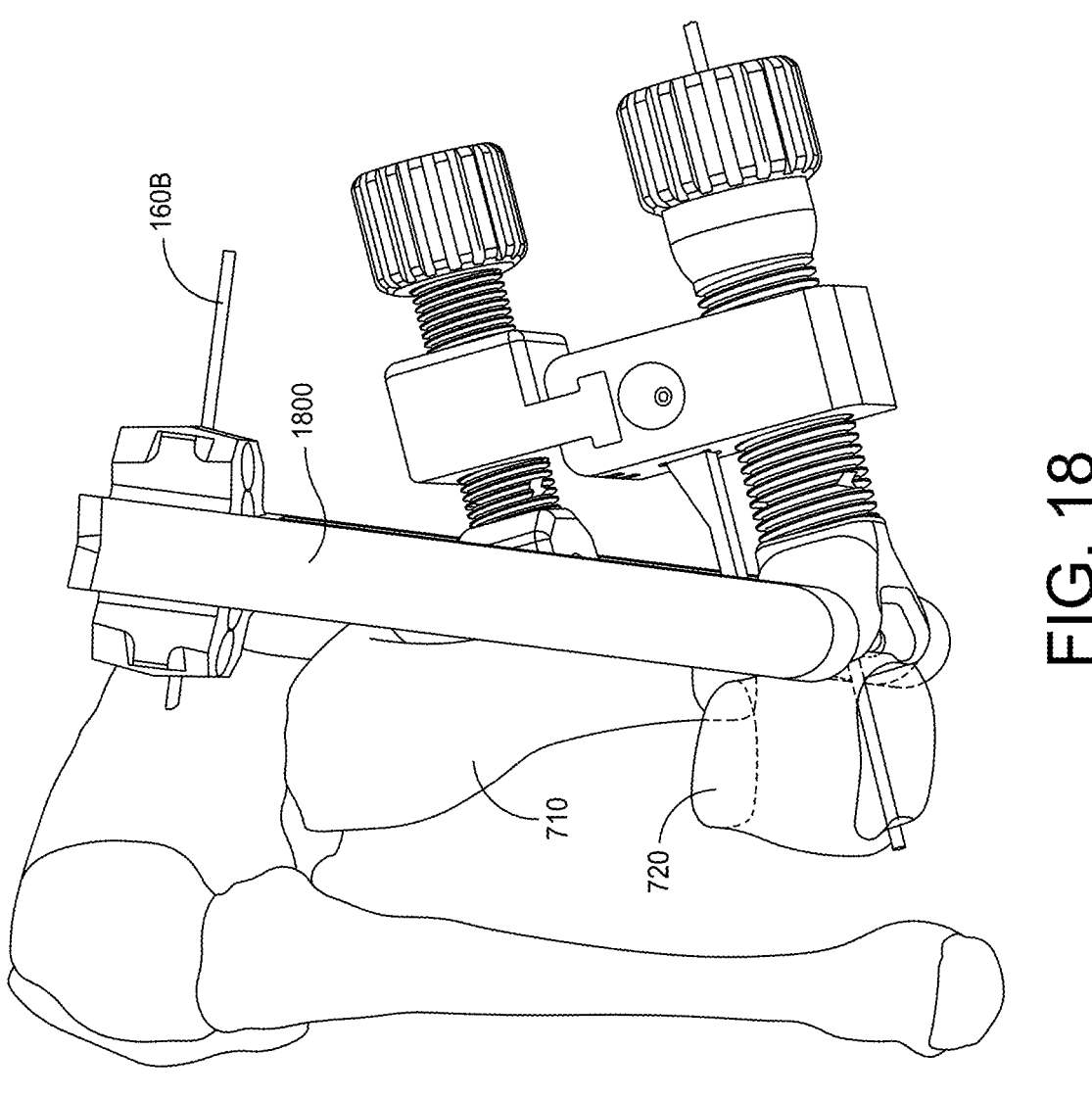

Referring to FIG. 18, another anchor pin 160B may be added through the targeting arm 1800 and into adjacent bone structure to aid in stabilizing the targeting arm 1800. This anchor pin 160B may have an olive feature to hold the target arm 1800 against the bone. Optionally, the user may bend the anchor pin 160B to accomplish the same stabilizing effect. Stabilizing the targeting arm 1800 against the foot allows assembly of the system 100 to continue. In this state, all of the components of the assembly are in place. The IM hook 113 is in intramedullary canal and held in place with an opposing force provided by the second screw mechanism 120 generated between where the second skin-interfacing wedge 124 interfaces the skin outside of the proximal fragment 710 and the joint of the first block 111 and the second block 121. The first screw mechanism 110 has provided a lateral force from the stabilized first block 111 to displace and shift the capital fragment 720 away from the proximal fragment 710 and into position to be fixated. The location of the shifted capital fragment 720 is stabilized by attaching one end of the targeting arm 130 to the first skin-interfacing wedge 114 and anchoring the other end of the targeting arm 1800 to the foot.

Figure 19:
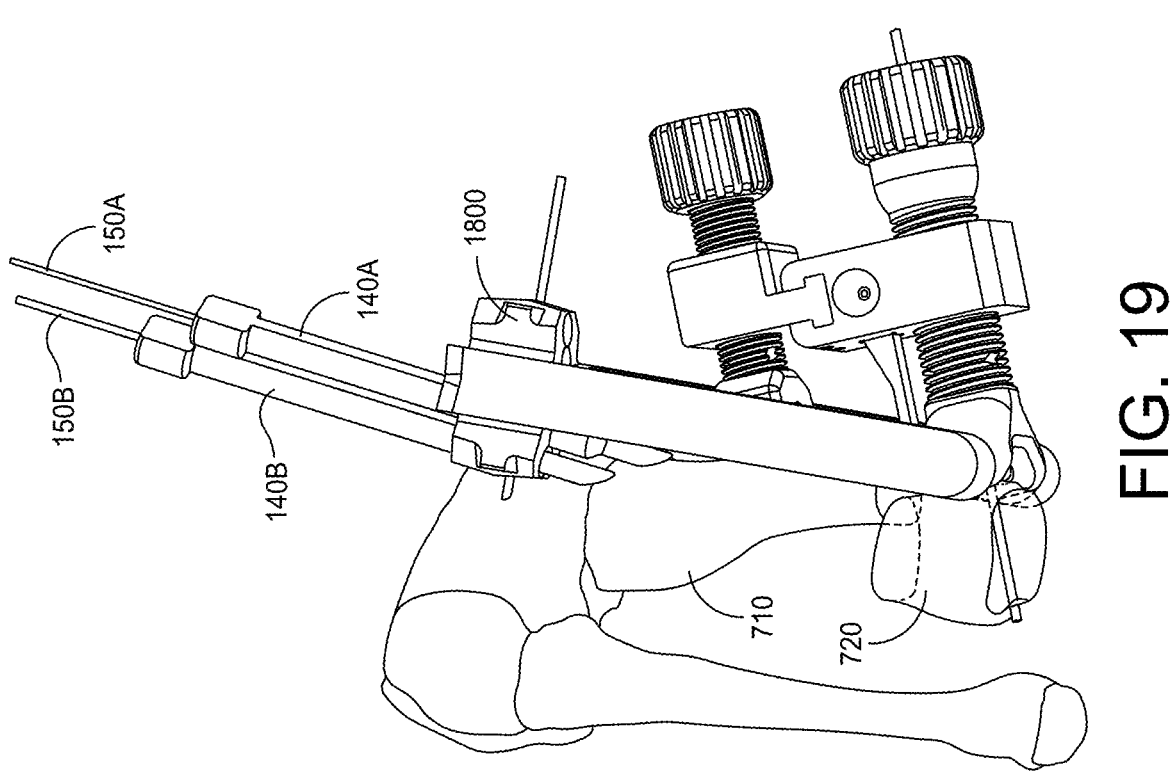

Because of the stability provided by the assembly shown in FIG. 18, FIG. 19 shows that appropriately-sized one or more wire sleeves 140A, 140B may be inserted into the guide holes of the targeting arm 1800. Appropriate fixation or K-wires 150A, 150B, one each corresponding to each of the wire sleeves 140A, 140B, maybe driven down the projected trajectory to predetermined target locations through the proximal fragment 710 and into the capital fragment 720 to complete assembly and fixation of the system 100. This position fixes the relative position of the capital fragment 720 to the proximal fragment 710. Once relative alignment of the bone fragments is achieved, the user may more permanently stabilize the bone orientation using screws, pins, plates, or any other suitable devices or techniques prior to disassembly and removal of the system 100 from the surgical field. Thus, the system 100 may be used to shift, stabilize, and target osteotomy fragments during minimally invasive osteotomy surgery.

Figure 20:
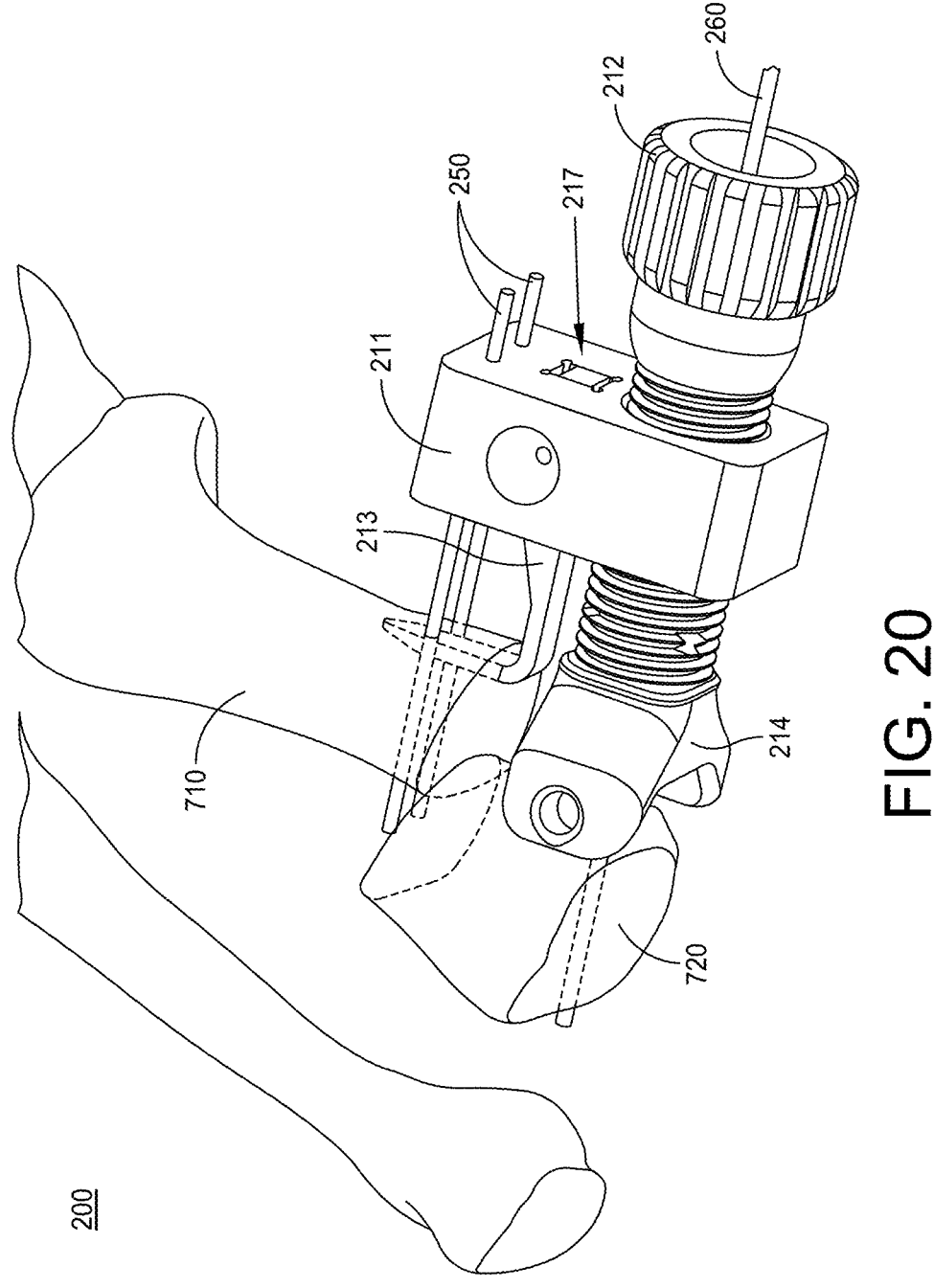
FIG. 20 shows a system according to another embodiment of the invention.

Referring to FIG. 20, another system 200 is provided in accordance with a further embodiment of the invention. The system 200 may use additional guide pins in place of a proximal second screw mechanism and targeting arm to facilitate a distal metatarsal 720 osteotomy for bunion correction via a minimally invasive surgical (MIS) procedure. System 200 may include a third block 211 that includes a threaded bore to accept a third screw 212. The third screw 212 may include a bore completely therethrough along a longitudinal axis that may be used to locate and guide an anchor pin 260. The system 200 may also include an IM member or hook 213 that may be attached to the third block 211. The third block 211 may include an aperture, window, or opening 217 that exposes a first end portion of the IM hook 213. The system 200 may also include a third skin-interfacing wedge 214 attached to an end of the third screw 212. FIG. 20 also shows that the third block 211 may include one or more through holes used to locate and guide additional anchor pins 250 to stabilize the system 200. As shown, the anchor pins 250 may be passed through the third block 211 and into the first metatarsal 710.

In use, after incision, the IM hook 213 may be inserted into the intramedullary (IM) canal of the proximal fragment of the patient's first metatarsal 710 while the third skin-interfacing wedge 214 is used to pivot the second system 200 against the patient's skin while the second system 200 is rotated such that a long-length portion of the IM hook 213 and a longitudinal axis through the system 200 are aligned substantially perpendicular to the first metatarsal 710. Anchor pins 250 may be used to further stabilize the system 200 in position. Optionally, the anchor pins 250 may be inserted prior to turning the third screw 212. Optionally, wire sleeves may be inserted into bore in the third block 211 and used to target and guide anchor pins 250. Optionally, the third block 211 may include a feature to join with the second screw mechanism 120 so that system 200 may be used along with the second screw mechanism 120 and a targeting arm.

An anchor pin 260 may then be inserted through the cannulated third screw 212 and the third skin-interfacing wedge 214 and into the capital fragment 720 to anchor the capital fragment 720. After the anchor pin 260 is inserted, the third screw 212 may be turned, enforcing lateralization of the capital fragment 720 which is stabilized against undesired elevation/planarization, inversion/eversion, and pronation/supination.

Once relative alignment of the bone fragments is achieved, the user may more permanently stabilize the bone orientation using screws, pins, plates, or any other suitable devices or techniques prior to disassembly and removal of the system 200. Optionally, the system 200 may be used in conjunction with a targeting arm as discussed above with respect to system 100.

Thus, the system 200 of the invention may be used to shift, stabilize, and target osteotomy fragments during minimally invasive osteotomy surgery.

It should be understood that the foregoing description is only illustrative of the invention. Various alternatives and modifications may be devised by those skilled in the art without departing from the invention. Accordingly, the invention is intended to embrace all such alternatives, modifications, and variances that fall within the scope of the appended claims.

What is claimed is:

1. A bone alignment system to correct a hallux valgus deformity comprising:

a main body including an intramedullary (IM) hook, the IM hook including a tapered end portion sized and configured to be inserted into an intramedullary canal of at least one of a first fragment or a second fragment of a bisected metatarsal; and a screw assembly including a screw threaded through the main body and a wedge shaped skin-interfacing portion attached to a first end of the screw, wherein the main body defines an aperture that extends through the main body and is sized and configured to guide a guide pin for anchoring the main body to the metatarsal.

2. The system of claim 1, wherein the IM hook is substantially L-shaped.

3. The system of claim 1, wherein the IM hook has a rectangular cross-sectional shape that includes a portion terminating at the tapered end.

4. The system of claim 1, wherein so that rotation of the screw is configured to pivot the system against a patient's skin such that a portion of the IM hook and a longitudinal axis through the screw are aligned substantially perpendicular to the first fragment or the second fragment.

5. The system of claim 1, wherein the screw is cannulated such that an anchor pin can be inserted though the screw and the skin-interfacing portion and into the metatarsal.

6. The system of claim 1, wherein the skin-interfacing portion is configured to be moved relative to the main body by rotating the screw.

7. The system of claim 1, wherein the main body is configured to pivot relative to the skin-interfacing portion when the skin-interfacing portion is against a patient's skin outside the metatarsal and the IM hook is disposed in an intramedullary canal of the metatarsal to change orientation of the second fragment with respect to the first fragment.

8. The system of claim 1, wherein the screw assembly further includes a head attached to a second end of the screw with a diameter that is larger than a diameter of a shaft of the screw and that can be used to grip the screw to provide a rotational force by at least one of a hand or a tool.

9. The system of claim 1, wherein the aperture is two apertures.

10. The system of claim 1, wherein the skin interfacing portion is arranged and configured to generate a lateral force against the metatarsal when the screw is rotated while the end portion of the IM hook is in the intramedullary canal.

11. A kit comprising:

the system of claim 1, and the guide pin.

12. A system comprising:

a body including a hook terminating in a tapered end and further including an end portion sized and configured to be inserted into an intramedullary canal of at least one fragment of a bisected metatarsal;

a screw disposed within a hole defined by the body, the screw including a wedge shaped skin-interfacing portion at a first end and a user-interface at a second end, wherein the screw defines an aperture that is sized and configured to receive a pin therethrough.

13. The system of claim 12, wherein the body defines an aperture that extends through the body and is sized configured to guide a guide pin for anchoring the body to the metatarsal.

14. The system of claim 13, wherein the body defines a plurality of apertures that extend through the body that are each sized and configured to guide a guide pin for anchoring the body to the metatarsal.

15. The system of claim 12, wherein the hook is substantially L-shaped.

16. The system of claim 12, wherein the hook has a rectangular cross-sectional shape that includes a portion terminating at the tapered end.

17. The system of claim 12, wherein rotation of the screw is configured to pivot the system against a patient's skin such that a portion of the hook and a longitudinal axis through the screw are aligned substantially perpendicular to the at least one fragment of the bisected metatarsal.

18. The system of claim 12, wherein the body is configured to pivot relative to the skin-interfacing portion when the skin-interfacing portion is against a patient's skin outside the metatarsal and the hook is disposed in the intramedullary canal to change orientation of a second fragment with respect to a first fragment of the at least one fragment of the bisected metatarsal.

19. The system of claim 12, wherein the skin interfacing portion is arranged and configured to generate a lateral force against the metatarsal when the screw is rotated while the end portion of the hook is in the intramedullary canal.

* * * * *